US010856916B2

(12) United States Patent
Kmiec, Jr. et al.

(10) Patent No.: US 10,856,916 B2
(45) Date of Patent: Dec. 8, 2020

(54) FLEXIBLE SHAFT GUIDE TUBE

(71) Applicant: DePuy Synthes Products, Inc., Raynham, MA (US)

(72) Inventors: Stanley J. Kmiec, Jr., West Chester, PA (US); Stanley J. Kmiec, III, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 53 days.

(21) Appl. No.: 16/191,590

(22) Filed: Nov. 15, 2018

(65) Prior Publication Data

US 2020/0155206 A1    May 21, 2020

(51) Int. Cl.
*A61B 17/72* (2006.01)
*A61B 17/16* (2006.01)
*A61B 17/17* (2006.01)

(52) U.S. Cl.
CPC ........ *A61B 17/7208* (2013.01); *A61B 17/164* (2013.01); *A61B 17/1717* (2013.01)

(58) Field of Classification Search
CPC .............. A61B 17/7233; A61B 17/725; A61B 17/1717; A61B 17/1753; A61B 17/921
See application file for complete search history.

(56) References Cited

U.S. PATENT DOCUMENTS

| | | | |
|---|---|---|---|
| 5,176,681 A * | 1/1993 | Lawes | A61B 17/744 606/64 |
| 5,215,090 A | 6/1993 | Hon et al. | |
| 6,419,678 B1 | 7/2002 | Asfora | |
| 8,679,120 B2 | 3/2014 | Frigg et al. | |
| 8,690,920 B2 | 4/2014 | Perez-Cruet et al. | |
| 9,050,164 B2 | 6/2015 | Chu et al. | |
| 9,308,031 B2 * | 4/2016 | Elghazaly | A61B 17/725 |
| 9,320,551 B2 * | 4/2016 | Frank | A61B 17/744 |
| 9,744,008 B2 | 8/2017 | Bassett et al. | |
| 9,943,346 B2 * | 4/2018 | Elghazaly | A61B 17/725 |
| 2002/0107578 A1 * | 8/2002 | Speitling | A61L 31/022 623/23.6 |
| 2006/0200160 A1 * | 9/2006 | Border | A61B 17/72 606/88 |
| 2007/0276382 A1 * | 11/2007 | Mikhail | A61B 17/1725 606/62 |
| 2008/0221577 A1 * | 9/2008 | Elghazaly | A61B 17/7241 606/64 |

(Continued)

*Primary Examiner* — Ellen C Hammond
(74) *Attorney, Agent, or Firm* — Fay Kaplun & Marcin, LLP

(57) ABSTRACT

A system for treating a bone includes an insertion device for an intramedullary nail. A first end includes a channel extending therethrough so that, when the insertion device is coupled to an intramedullary nail, the channel of the device is aligned with and in communication with a channel of the nail. The system also includes a guide sleeve extending from a proximal end to a distal end and including a first bend extending along a portion of a length thereof so that a longitudinal axis of a distal portion of the sleeve is angled with respect to a longitudinal axis of a remaining portion of the sleeve. In an operative position, the distal end of the sleeve is inserted into the channel of the device and the remaining portion of the sleeve extends toward a lateral side of a bone being treated.

20 Claims, 4 Drawing Sheets

(56) References Cited

U.S. PATENT DOCUMENTS

| | | | |
|---|---|---|---|
| 2008/0294164 A1* | 11/2008 | Frank | A61B 17/7233 606/64 |
| 2009/0048600 A1* | 2/2009 | Matityahu | A61B 17/7241 606/62 |
| 2012/0197255 A1* | 8/2012 | Elghazaly | A61B 17/725 606/64 |
| 2014/0058392 A1* | 2/2014 | Mueckter | A61B 17/744 606/64 |
| 2014/0214045 A1* | 7/2014 | Felder | A61B 17/72 606/104 |
| 2018/0092674 A1* | 4/2018 | McDaniel | A61B 17/7225 |
| 2018/0250042 A1* | 9/2018 | Sato | A61B 17/7233 |

\* cited by examiner

FLEXIBLE SHAFT GUIDE TUBE

BACKGROUND

Some fractures of long bones may be treated by placing the bone into corrective alignment and inserting an intramedullary nail into a medullary canal of the aligned bone. In particular, for a trochanteric fixation treatment, upon insertion of an intramedullary nail into the medullary canal of the trochanter, a fixation nail may be inserted laterally through the intramedullary nail into a condylar portion of the bone. A plunger, housed within a channel of the intramedullary nail, proximally of the fixation nail, may interface with the fixation nail to permit lateral migration of the fixation nail.

SUMMARY

The present disclosure is directed to a system for treating a bone, comprising an insertion device for an intramedullary nail, the insertion device extending from a first end configured to be connected to a proximal end of an intramedullary nail to a second end, the first end including a channel extending therethrough so that, when the insertion device is coupled to an intramedullary nail, the channel of the insertion device is aligned with and in communication with a channel of the intramedullary nail, and a guide sleeve extending from a proximal end to a distal end and including a first bend extending along a portion of a length thereof so that a longitudinal axis of a distal portion of the guide sleeve is angled with respect to a longitudinal axis of a remaining portion of the guide sleeve, the guide sleeve configured to be coupled to the insertion device so that, in an operative position, the distal end of the guide sleeve is inserted into the channel of the insertion device and the remaining portion of the guide sleeve extends toward a lateral side of a bone being treated, a channel of the guide sleeve aligned with and in communication with the channel of the insertion device in the operative position.

The present disclosure is also directed to a system for treating a bone, comprising an intramedullary nail extending longitudinally from a proximal end to a distal end and including a transverse opening extending therethrough, the transverse opening configured to receive a fixation element therein, the intramedullary nail including a locking mechanism housed within a channel of the intramedullary nail proximal of the transverse opening and movable between a locking configuration, in which a locking portion of the locking mechanism extends into transverse opening, and a non-locking configuration, in which the locking portion does not extend into the transverse opening, an insertion device extending from a first end coupleable to the proximal end of the insertion device to a second end, the first end including a channel extending therethrough so that, when the insertion device is coupled to the intramedullary nail the channel of the insertion device is aligned and in communication with the channel of the intramedullary nail. The system also comprises a guide sleeve extending from a proximal end to a distal end and including a guiding channel extending therethrough, the guide sleeve including a first bend along a portion thereof so that a longitudinal axis of a distal portion of the guide sleeve is angled with respect to a remaining portion of the guide sleeve, the guide sleeve configured to be coupled to the insertion device so that, in an operative position, the distal end is received within the channel of the insertion device and the remaining portion extends toward a lateral side of a bone being treated, and a flexible driver shaft sized and shaped to be inserted through the guiding channel and into the channel of the intramedullary nail so that a distal end of the flexible driver shaft is engagable with the locking mechanism to move the locking mechanism between the locking and the non-locking configurations.

BRIEF DESCRIPTION

DETAILED DESCRIPTION

Figure 1:
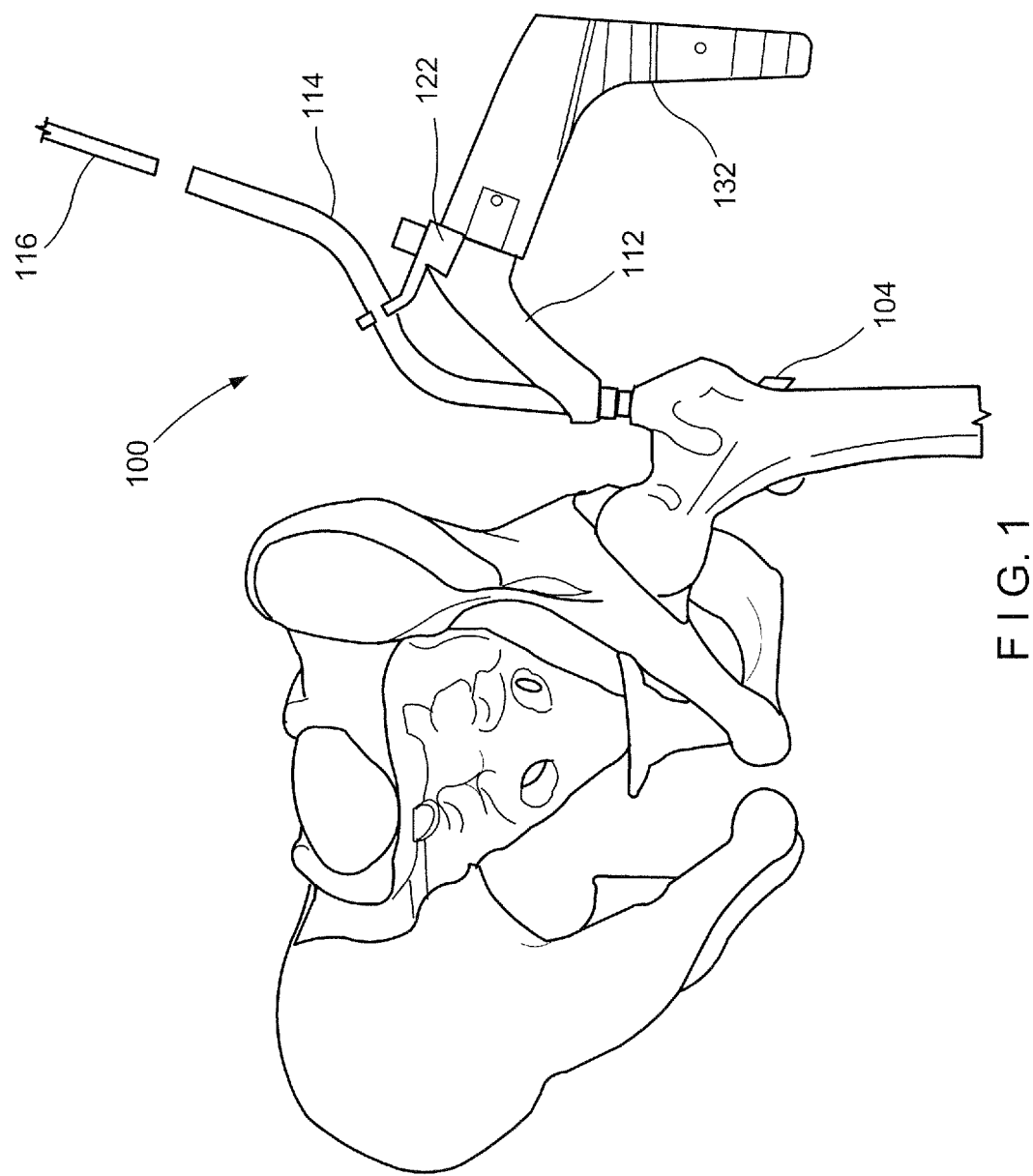
FIG. 1 shows a perspective view of a system according to an exemplary embodiment of the present disclosure.

The present invention may be further understood with reference to the following description and the appended drawings, wherein like elements are referred to with the same reference numerals. The exemplary embodiments of the present disclosure refer to a guide tube sized and shaped to be attached to an insertion device of a fixation system. In particular, the exemplary embodiments describe a guide tube that is curved to avoid soft tissue impingement on a medial side of the aiming handle, which may cause difficulty during insertion of a flexible driver shaft through a proximal opening of an intramedullary nail. Although the exemplary embodiments show and describe a trochanteric fixation system for a femur, it will be understood by those of skill in the art that the system of the present disclosure may be similarly utilized in other areas of the body.

Figure 2:
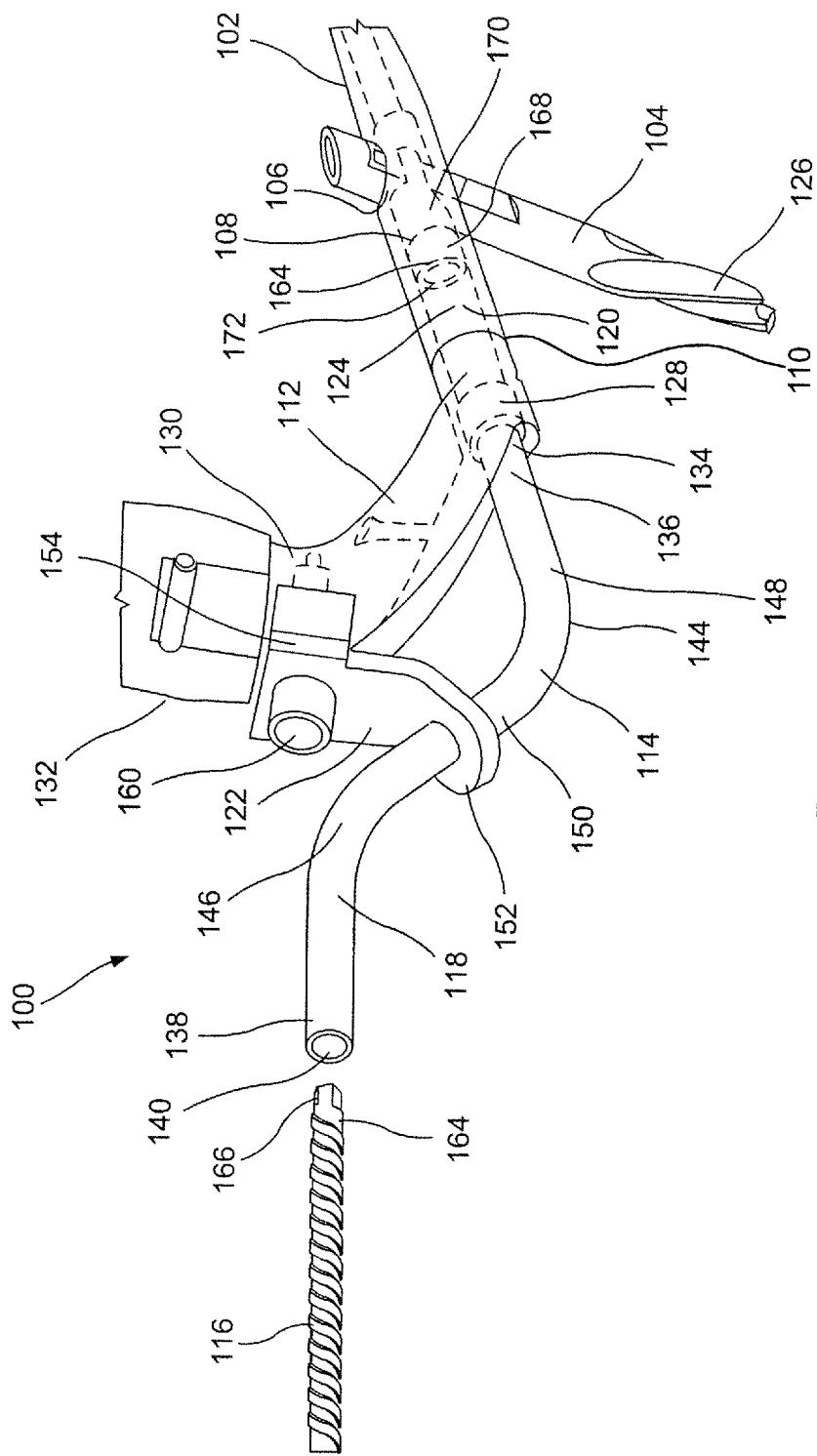
FIG. 2 shows a perspective view of an assembly of the system of FIG. 1.
Figure 3:
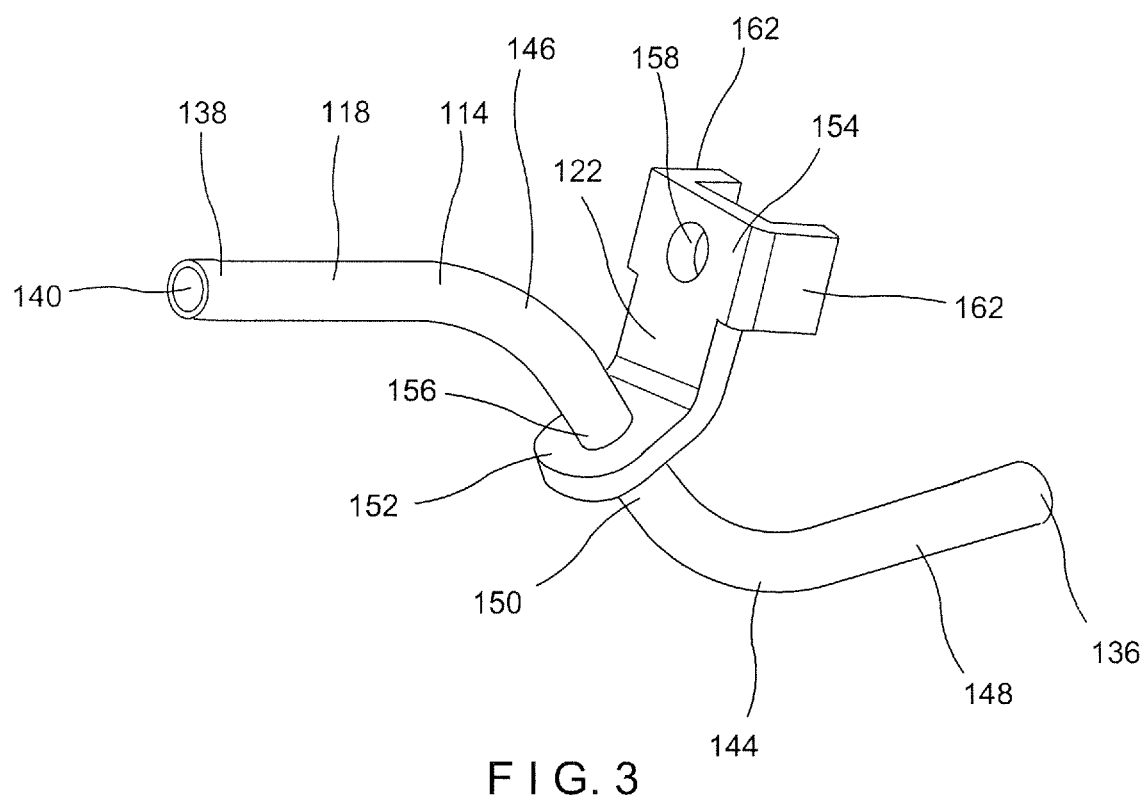
FIG. 3 shows a perspective view of a guide sleeve and bracket of the system of FIG. 1.

As shown in FIGS. 1-3, a bone fixation system 100 according to an exemplary embodiment of the present disclosure comprises an intramedullary nail 102 configured to be inserted into a medullary canal of a bone (e.g., femur), a fixation element 104 sized and shaped to be inserted through a transverse opening 106 of the intramedullary nail 102 at an angle relative to a longitudinal axis of the intramedullary nail 102, and a locking mechanism 108 housed within a channel 124 of the intramedullary nail 102 for locking of the fixation element 104 within the opening 106. The system 100 further comprises an insertion device 112 coupleable to the intramedullary nail 102 for insertion thereof and a guide sleeve 114 mountable to the insertion device 112 for guiding a flexible driving shaft 116 (e.g., a flexible screwdriver) therethrough to the proximal opening 110. The guide sleeve 114 is specifically sized to accommodate the flexible driver shaft 116 and shaped to avoid soft tissue impingement on a medial side of the insertion device 112. In particular, the guide sleeve 114 may be bent laterally such that a proximal portion 118 thereof, through which the flexible drive shaft 116 is to be inserted, is spaced laterally from a longitudinal axis of the intramedullary nail 102 to avoid soft tissue on the medial side of the insertion device 112, which in some cases, may cause difficulty during insertion of the flexible driver shaft 116. The guide sleeve 114 may be mounted to the insertion device 112 via a bracket 122, which fixes the guide sleeve 114 in a desired position relative to the insertion device 112 so that, when the guide sleeve 114 is mounted to the insertion device 112 upon insertion of the intramedullary nail 102, the proximal portion 118 of the guide sleeve 114 extends toward and away from a lateral side of the patient's body.

As would be understood by those skilled in the art, the intramedullary nail 102 extends along a longitudinal axis from a proximal end 120 to a distal end (not shown) and is sized and shaped for insertion into a medullary canal of a long bone such as, for example, a femur. A channel 124 extends through at least a portion of the intramedullary nail 102 from the proximal opening 110 along the longitudinal axis thereof. The transverse opening 106 extends through the intramedullary nail 102 along an axis extending at an angle relative to the longitudinal axis of the intramedullary nail 102 so that a fixation element 104 inserted therethrough will pass into, for example, a head portion of the bone, in an operative configuration. The transverse opening 106 is in communication with the channel 124. The locking mechanism 108 is housed within the channel 124, proximally of the transverse opening 106 and is movable between a non-locking configuration, in which the locking mechanism 108 does not engage the fixation element 104 received within the transverse opening 106, and a locking configuration, in which the locking mechanism 108 extends into the transverse opening 106 to engage a portion of the fixation element 104 received therein to lock the fixation element 104 in a desired position relative thereto.

The fixation element 104 is sized and shaped to be inserted into the transverse opening 106 along, for example, a femoral neck axis so that a distal locking portion 126 thereof extends into a head portion of the bone. The distal locking portion 126 may include, for example, helical blades or threads. As would be understood by those skilled in the art, in one embodiment, the fixation element 104 is configured to permit lateral migration (but not medial migration) of at least a portion of the fixation element 104 as the bone heals. The fixation element 104 may have any number of configurations. In one example, the fixation element 104 includes a single element including a proximal portion slidably movable within the transverse opening 106 along the axis along which the transverse opening 106 extends and the distal portion locking portion 126 which extends into the head portion. In another example, the fixation element 104 includes telescoping inner and outer portions, in which the inner portion is slidably relative to the outer portion.

As described above, the locking mechanism 108 is movably housed within the channel 124 proximally of the transverse opening 106 to selectively engage and disengage a portion of the fixation element 104 received within the transverse opening 106, when moved between the locking and non-locking configurations. For example, in the locking configuration, a portion of the locking mechanism 108 may be moved into transverse opening 106 to engage a portion of the fixation element 104 received therein. In the locking configuration, the locking mechanism 108 engages the fixation element 104 to prevent rotation thereof relative to the axis of the transverse opening 106. In the non-locking configuration, the locking mechanism 108 may be moved out of the transverse opening 106 so that the fixation element 104 may be moved longitudinally along the axis of the transverse opening 106.

In one embodiment, the locking mechanism 108 includes a proximal portion 168 threadedly engaged to the channel 124 to move the locking mechanism 108 between the non-locking and the locking configurations. In the locking configuration, a portion of the locking mechanism 108 is moved into engagement with a portion of the fixation element 104 to prevent rotation of the fixation element 104 within the transverse opening 106. For example, when the proximal portion 168 is rotated in a first direction, a distal portion 170 thereof moves into engagement with the fixation element 104, and when the proximal portion 168 is rotated in a second direction, the distal portion 170 moves out of engagement with the fixation element 104. It will be understood by those of skill in the art that the locking mechanism 108 may have any of a number of configurations so long as the locking mechanism 108 may be moved in and out of engagement with the fixation element 104 received within the transverse opening 106.

The insertion device 112 is bent and/or curved along its length between a first end 128 configured to be coupled to the proximal end 120 of the intramedullary nail 102 and a second end 130, which is coupled to a handle member 132 configured to be gripped by a user (e.g., surgeon) during insertion of the intramedullary nail 102. The first end 128 also includes a channel 134 extending therethrough so that, when the first end 128 is coupled to the intramedullary nail 102, the channel 134 of the insertion device 112 is coaxially aligned with the channel 124 of the intramedullary nail 102. In an operative position, the handle portion 132 extends on a lateral side of the bone, and thereby of the intramedullary nail 102, so that the user may grip the handle portion 132 as the intramedullary nail 102 is being inserted into the bone.

As described above, the guide sleeve 114 is configured to be mounted to the insertion device 112 to guide a flexible driver shaft 116 therethrough and into the channel 124 to drive the locking mechanism 108 housed therein from the non-locking to the locking configuration. The guide sleeve 114 extends from a distal end 136 to a proximal end 138 and includes a channel 140 through which the flexible driver shaft 116 may be guided. In one embodiment, the guide sleeve 114 may include a first bend 144 and a second bend 146, curvatures of the first bend 144 and the second bend 146 extending along a common plane to define a distal portion 148, a middle portion 150 and the proximal portion 118 of the guide sleeve 114. The first bend 144 extends along a portion of a length of the guide sleeve 114 so that a longitudinal axis of the distal portion 148 is angled with respect to a longitudinal axis of the middle portion 150. The second bend 146 extends along a portion of a length of the guide sleeve 114 so that the longitudinal axis of the middle portion 150 is angled with respect to the proximal portion 118. Thus, when the guide sleeve 114 is mounted to the insertion device 112 via, for example, the bracket 122, the proximal portion 118 of the guide sleeve 114 extends along and/or toward the lateral side of the patient body, away from any soft tissue pressing against a medial side of the insertion device 112 which may have otherwise caused difficulty when inserting a driver for driving the locking mechanism 108. Each of the first and second bends 144, 146 may be bent at an angle ranging from between 90 degrees and less than 180 degrees with a radius of approximately 25 mm to 1000 mm.

As described above, the guide sleeve 114 may be mounted to the insertion device 112 via the bracket 122. The bracket 122 includes a first portion 152 configured to be coupled to the guide sleeve 114 and a second portion 154 configured to be coupled to the insertion device 112. In particular, the first portion 152 may include an opening 156 extending through the first portion 152, the opening 156 is sized and shaped to receive the guide sleeve 114 therethrough. The second portion 154 includes an opening 158 extending therethrough, the opening 158 configured to receive a screw 160 therein for fixing the bracket 122 to the insertion device 112. The second portion 154 may further include a pair of mounting arms 162 extending laterally therefrom, the mounting arms 162 specifically sized and shaped to extend over and engage the second end 130 of the insertion device 112 so that, when the mounting arms 162 engage the second end 130 and the screw 160 is inserted through the opening 158 to fix the bracket 122 to the insertion device 112, the bracket 122 cannot be rotated and/or otherwise moved relative to the insertion device 112.

In one embodiment, the guide sleeve 114 is assembled with the bracket 122 by inserting the guide sleeve 114 through the opening 156 of the first portion 152 until the first portion 152 extends about a portion of the guide sleeve 114 proximal of the first bend 144. When the second portion 154 is mounted to the second end 130 of the insertion device 112, the distal end 136 of the guide sleeve 114 is received within the channel 134 at the first end 128 of the insertion device 112 so that the channel 140 of the guide sleeve 114 is in aligned with and/or in communication with the channel 124 of the intramedullary nail 102.

Although the bracket 122 is shown and described as being a separate component, it will be understood by those of skill in the art that the bracket 122 may also be integrally formed with the guide sleeve 114 so that the guide sleeve 114 and the bracket 122 need not be assembled prior to mounting of the bracket 122 to the insertion device 112. It will also be understood by those of skill in the art that the screw 160, when inserted through the opening 158 of the second portion 154 to mount the bracket 122 to the insertion device 112, engages a corresponding opening in the insertion device 112. This opening may, for example, be an existing opening in currently available insertion devices 112, which is utilized for coupling the insertion device 112 to the handle member 132.

The flexible driver shaft 116 extends longitudinally from a proximal end (not shown) to a distal end 164 including a connecting member 166 sized and shaped to be received within a corresponding recess 172 of the locking mechanism 108. For example, the connecting member 166 may have a substantially hexagonal shape to be received within a hex-shaped recess of the locking mechanism 108. The flexible driver shaft 116 is configured to be sufficiently flexible so that the flexible driver shaft 116 may be inserted through the guide sleeve 114, past the first and second bends 144, 146, until the connecting member 166 engages the recess 172 of the locking mechanism 108. The flexible driver shaft 116 is also configured so that a torque applied to the proximal end thereof results in a corresponding torsion at the distal end 164 to rotate the proximal portion 168 of the locking mechanism 108 and move the locking mechanism 108 between the non-locking and locking configurations.

In use, the intramedullary nail 102 is inserted into the medullary canal of, for example, a femoral bone, using the insertion device 112, using any known technique as will be understood by those of skill in the art. Upon insertion of the intramedullary nail 102, the fixation element 104 is inserted through the transverse opening 106 into the femoral head. To fix the fixation element 104 in a locked configuration, the guide sleeve 114 may be mounted to the insertion device 112 using the bracket 122, as described above. Once the guide sleeve 114 has been mounted to the insertion device 112, the flexible driver shaft 116 is inserted through the channel 140 of the guide sleeve 114, past the first and second bends 144, 146, until the connecting member 166 engages the recess 172 of the proximal portion 168. The flexible driver shaft 116 may then be used to move the locking mechanism from the non-locking configuration to the locking configuration.

Figure 4:
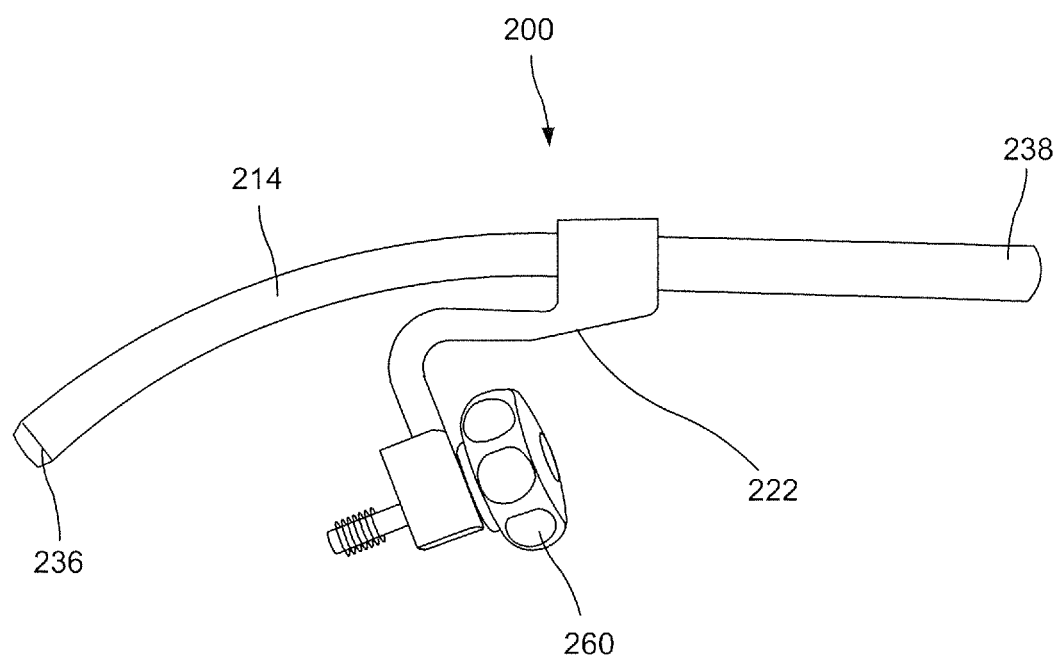
FIG. 4 shows a perspective view of a system according to another exemplary embodiment of the present disclosure.
Figure 5:
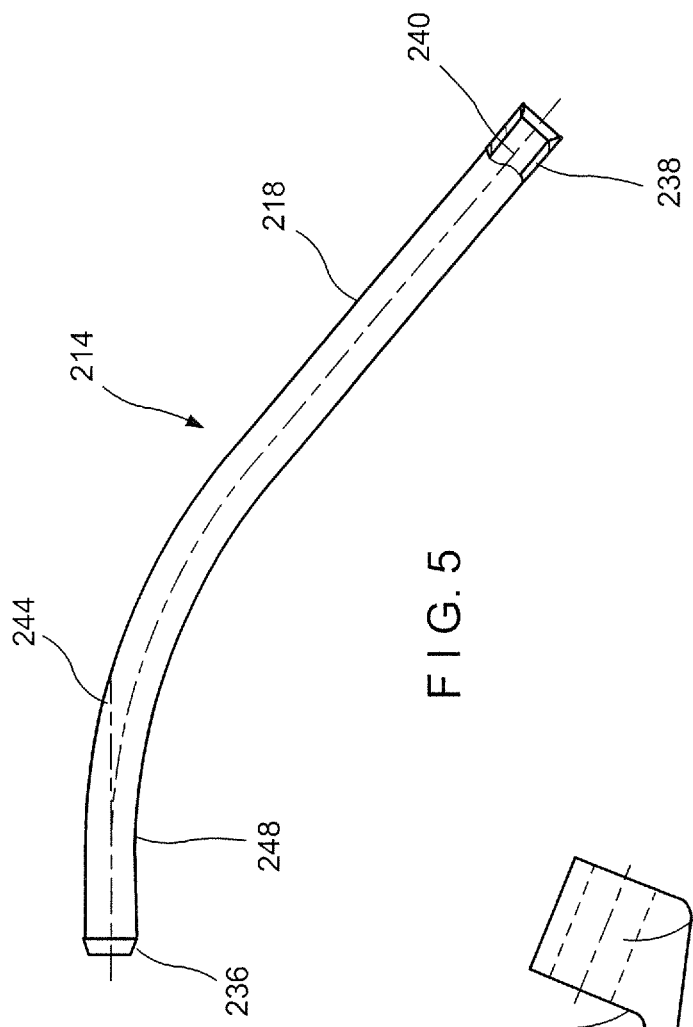
FIG. 5 shows a longitudinal side view of a guide sleeve of the system of FIG. 4.
Figure 6:
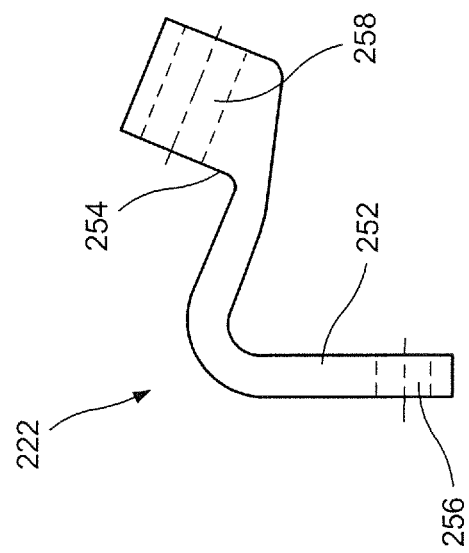
FIG. 6 show a longitudinal side view of a bracket of the system of FIG. 4.

Although the guide sleeve 114 is shown and described above as including first and second bends 144, 146, the guide sleeve 114 may have any of a variety of shapes and configurations so long as a proximal portion 118 extends laterally away from a longitudinal axis of the nail when assembled with the insertion device 112 in an operative configuration. For example, as shown in FIGS. 4-6, a system 200 according to another exemplary embodiment may be substantially similar to the system 100 described above. In particular, the system 200 comprises a guide sleeve 214 that is configured to be mounted to the insertion device 112, as described above with respect to the system 100, for guiding the flexible driver shaft 116. The guide sleeve 214 may be utilized with the insertion device 112, the flexible driver shaft 116, the intramedullary nail 102 and the locking mechanism 108, as described above with respect to the system 100. The guide sleeve 214 functions in substantially the same manner as the guide sleeve 114, except as noted below.

Similarly to the guide sleeve 114, the guide sleeve 214 extends from a distal end 236 to a proximal end 238 and includes a channel 240 extending longitudinally therethrough. The guide sleeve 214 may be mounted to the insertion device 112 via a bracket 222, which is substantially similar to the bracket 122 described above. Rather than two bends, however, the guide sleeve 214 includes a single bend 244 extending along portion of a length of the guide sleeve 214 so that a longitudinal axis of a proximal portion 218 of the guide sleeve 214 extends at an angle relative to a longitudinal axis of a distal portion 248 of the guide sleeve 214. Thus, when the guide sleeve 214 is mounted to the insertion device 112 so that the distal end 236 is received within the channel 134 in alignment with and/or in communication with the channel 124 of the intramedullary nail 102 that has been inserted into a medullary canal of a bone, the proximal portion 218 extends toward a lateral side of the patient body, away from any tissue impingement that may interfere with the insertion of a driver for driving the locking mechanism 108 of the intramedullary nail 102 from a non-locking to a locking configuration.

In one exemplary embodiment, the bend 244 of the guide sleeve 214 is configured so that the longitudinal axis of the proximal portion 218 extends at an angle of between 90 degrees and less than 180 degrees relative to the longitudinal axis of the distal portion 248 and, in a particular embodiment, extends at an angle of approximately 40 degrees. A bending radius between proximal and distal portions 218, 248 may range from 25 mm to 1000 mm.

The bracket 222 may be substantially similar to the bracket 122 of the system 100, including a first portion 252 configured to be coupled to the guide sleeve 214 and a second portion 254 to be mounted and engaged to the second end 130 of the insertion device 112. The first portion 252 includes an opening 256 for receiving the guide sleeve 214 and the second portion 254 includes an opening 258 configured to receive a screw 260 for fixing the bracket 222 to the insertion device 112. Similarly to the bracket 122, the first portion 252 may be coupled to the guide sleeve 214 so that the first portion 252 extends about a portion of the guide sleeve 214 proximal of the bend 244. When the guide sleeve 214 is assembled with the bracket 222 and the bracket 222 is mounted to the insertion device 112, the distal end 236 of the guide sleeve 214 is received within the channel 134 of the insertion device 112 so that the flexible driver shaft 116 may be inserted through the guide sleeve 214 into the channel 124 of the intramedullary nail to drive the locking mechanism 108 from the non-locking configuration to the locking configuration.

It will be understood by those of skill in the art that modifications and variations may be made in the structure and methodology of the present invention, without departing from the spirit and scope of the invention. Thus, it is intended that the present invention cover the modifications and variations of the invention, provided that they come within the scope of the appended claims and their equivalents.

What is claimed is:

1. A system for treating a bone, comprising:
an insertion device for an intramedullary nail, the insertion device extending from a first end configured to be connected to a proximal end of the intramedullary nail to a second end, the first end including a channel extending therethrough so that, when the insertion device is coupled to the intramedullary nail, the channel of the insertion device is aligned with and in communication with a channel of the intramedullary nail; and
a guide sleeve extending from a proximal end to a distal end and including a first bend extending along a portion of a length thereof so that a longitudinal axis of a distal portion of the guide sleeve is angled with respect to a longitudinal axis of a remaining portion of the guide sleeve, the guide sleeve configured to be coupled to the insertion device so that, in an operative position, the distal end of the guide sleeve is inserted into the channel of the insertion device and the remaining portion of the guide sleeve extends toward a lateral side of a bone being treated, a channel of the guide sleeve aligned with and in communication with the channel of the insertion device in the operative position.

2. The system of claim 1, further comprising a flexible driver shaft sized and shaped to be inserted through the guide sleeve.

3. The system of claim 1, further comprising a bracket configured to couple the guide sleeve to the insertion device, the bracket including a first portion couplable to the guide sleeve and a second portion mountable over a portion of the insertion device to fix the guide sleeve to the insertion device in the operative position.

4. The system of claim 3, wherein the first portion of the bracket includes an opening sized and shaped to receive the guide sleeve therein.

5. The system of claim 3, wherein the second portion of the bracket includes an opening configured to receive a screw for fixing the bracket to the insertion device.

6. The system of claim 3, wherein the bracket is integrally formed with the guide sleeve.

7. The system of claim 3, wherein, in the operative position, the first portion of the bracket extends about a portion of the guide sleeve proximal of the first bend.

8. The system of claim 3, wherein the second portion of the bracket includes mounting arms sized, shaped and configured to engage the insertion device so that, when the bracket is fixed to the insertion device, the bracket is non-rotatable with respect to the insertion device.

9. The system of claim 1, wherein the guide sleeve includes a second bend along the remaining portion thereof, the remaining portion including a proximal portion of the guide sleeve and a middle portion extending between the proximal and distal portions of the guide sleeve, a longitudinal axis of the middle portion being angled with respect to the longitudinal axis of the distal portion and a longitudinal axis of the proximal portion angled with respect to the longitudinal axis of the middle portion.

10. The system of claim 9, wherein the first and second bends extend along a common plane.

11. A system for treating a bone, comprising:
an intramedullary nail extending longitudinally from a proximal end to a distal end and including a transverse opening extending therethrough, the transverse opening configured to receive a fixation element therein, the intramedullary nail including a locking mechanism housed within a channel of the intramedullary nail proximal of the transverse opening and movable between a locking configuration, in which a locking portion of the locking mechanism extends into the transverse opening, and a non-locking configuration, in which the locking portion does not extend into the transverse opening;
an insertion device extending from a first end coupleable to the proximal end of the insertion device to a second end, the first end including a channel extending therethrough so that, when the insertion device is coupled to the intramedullary nail the channel of the insertion device is aligned and in communication with the channel of the intramedullary nail;
a guide sleeve extending from a proximal end to a distal end and including a guiding channel extending therethrough, the guide sleeve including a first bend along a portion thereof so that a longitudinal axis of a distal portion of the guide sleeve is angled with respect to a remaining portion of the guide sleeve, the guide sleeve configured to be coupled to the insertion device so that, in an operative position, the distal end is received within the channel of the insertion device and the remaining portion extends toward a lateral side of a bone being treated; and
a flexible driver shaft sized and shaped to be inserted through the guiding channel and into the channel of the intramedullary nail so that a distal end of the flexible driver shaft is engagable with the locking mechanism to move the locking mechanism between the locking and the non-locking configurations.

12. The system of claim 11, further comprising a bracket configured to couple the guide sleeve to the insertion device, the bracket including a first portion couplable to the guide sleeve and a second portion mountable over the second end of the insertion device to fix the guide sleeve to the insertion device in the operative position.

13. The system of claim 12, wherein the first portion of the bracket includes an opening sized and shaped to receive the guide sleeve therein.

14. The system of claim 12, wherein the second portion of the bracket includes an opening configured to receive a screw for fixing the bracket to the insertion device.

15. The system of claim 12, wherein the bracket is integrally formed with the guide sleeve.

16. The system of claim 12, wherein, in the operative position, the first portion of the bracket extends about a portion of the guide sleeve proximal of the first bend.

17. The system of claim 12, wherein the second portion of the bracket includes mounting arms sized, shaped and configured to engage the insertion device so that, when the bracket is fixed to the insertion device, the bracket is non-rotatable with respect to the insertion device.

18. The system of claim 11, wherein the guide sleeve includes a second bend along the remaining portion thereof, the remaining portion including a proximal portion of the guide sleeve and a middle portion extending between the proximal and distal portions of the guide sleeve, a longitudinal axis of the middle portion being angled with respect to the longitudinal axis of the distal portion and a longitudinal axis of the proximal portion angled with respect to the longitudinal axis of the middle portion.

19. The system of claim 18, wherein the first and second bends extend along a common plane.

20. The system of claim 11, further comprising a fixation element insertable through the transverse opening of the intramedullary nail, wherein, when the fixation element is inserted in the transverse opening, the locking mechanism engages the fixation element in the locking configuration to prevent rotation of the fixation element about a central axis thereof.

* * * * *